United States Patent
Deluca et al.

(10) Patent No.: US 8,759,328 B2
(45) Date of Patent: Jun. 24, 2014

(54) ONCE-A-WEEK ADMINISTRATION OF 25-HYDROXY VITAMIN $D_3$ TO SUSTAIN ELEVATED STEADY-STATE PHARMACOKINETIC BLOOD CONCENTRATION

(75) Inventors: Hector F. Deluca, Deerfield, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 187 days.

(21) Appl. No.: 12/672,190

(22) PCT Filed: Jul. 24, 2009

(86) PCT No.: PCT/US2009/051664
§ 371 (c)(1),
(2), (4) Date: Jan. 14, 2011

(87) PCT Pub. No.: WO2010/011906
PCT Pub. Date: Jan. 28, 2010

(65) Prior Publication Data
US 2011/0105444 A1  May 5, 2011

Related U.S. Application Data

(60) Provisional application No. 61/083,223, filed on Jul. 24, 2008.

(51) Int. Cl.
*A61K 31/593* (2006.01)
*A61K 31/592* (2006.01)
*A61P 3/02* (2006.01)

(52) U.S. Cl.
USPC ........................................................ 514/167

(58) Field of Classification Search
USPC .................................................. 514/167, 552
See application file for complete search history.

(56) References Cited

U.S. PATENT DOCUMENTS

| | | | |
|---|---|---|---|
| 3,607,888 | A | 9/1971 | DeLuca et al. |
| 8,207,149 | B2 * | 6/2012 | Tabash et al. .................. 514/167 |

(Continued)

OTHER PUBLICATIONS

E M Poskitt et al. (British Medical Journal, 1979, 1, 221-223).*

(Continued)

*Primary Examiner* — Sabiha N Qazi
(74) *Attorney, Agent, or Firm* — Quarles & Brady LLP

(57) ABSTRACT

An oral dosage form comprising a single dose of 25-hydroxy-vitamin $D_3$ sufficient to elevate the serum level in a human to a concentration in the range of 30 ng/ml to 200 ng/ml for at least 7 days and a pharmaceutically suitable oral carrier system, wherein subsequent single doses at least every 7 days are sufficient to sustain the serum level in a human to a concentration in the range of 30 ng/ml to 200 ng/ml at steady-state pharmacokinetics is disclosed. A method of elevating and sustaining the blood level concentration of 25-hydroxy-vitamin $D_3$ in a human in need thereof comprising orally administering or parenterally administering by injection or infusion, at least once every 7 days, a single dose of 25-hydroxy-vitamin $D_3$ sufficient to elevate the serum level in a human to a concentration in the range of 30 ng/ml to 200 ng/ml for at least 7 days, wherein the single doses orally administered at least every 7 days are sufficient to sustain the serum level in a human to a concentration in the range of 30 ng/ml to 200 ng/ml at steady-state pharmacokinetics is disclosed. The human in need thereof may be a human deficient in vitamin D having a serum level concentration of 25-hydroxy-vitamin $D_3$ less than 30 ng/ml.

41 Claims, 10 Drawing Sheets

(56) References Cited

U.S. PATENT DOCUMENTS

| | | | |
|---|---|---|---|
| 8,329,677 B2* | 12/2012 | Bishop et al. | 514/167 |
| 8,361,488 B2* | 1/2013 | Bishop et al. | 424/422 |
| 8,592,401 B2* | 11/2013 | Petkovich et al. | 514/167 |
| 2003/0195171 A1 | 10/2003 | Daifotis et al. | |
| 2005/0003004 A1 | 1/2005 | Vehring et al. | |
| 2005/0101576 A1 | 5/2005 | Whitehouse et al. | |
| 2009/0176748 A1* | 7/2009 | Tabash et al. | 514/167 |
| 2009/0311316 A1* | 12/2009 | Bishop et al. | 424/456 |
| 2010/0120728 A1* | 5/2010 | Petkovich et al. | 514/168 |
| 2011/0039810 A1* | 2/2011 | Buck et al. | 514/168 |
| 2013/0137663 A1* | 5/2013 | Messner et al. | 514/168 |
| 2013/0178451 A1* | 7/2013 | Bishop et al. | 514/168 |

OTHER PUBLICATIONS

Vin Tangpricha (Am. J. Med., Jun. 1, 2002, 112(8), 659-662).*
Shamik J. Parikh (The Journal of Clinical Endocrinology and Metabolism (89, (3):1196-1199).*
Heaney, R. P., et al., 25-Hydroxylation of vitamin D3: relation to circulating vitamin D3 under various input conditions, Am. J. Clin. Nutr. 87(6):1738-1742, 2008.
PCT International Search Report and Written Opinion, PCT/US2009/051664, Sep. 1, 2009.
Blunt, J. W., et al., 25-Hydroxycholecalciferol. A Biologically Active Metabolite of Vitamin D3, Biochemistry 7:3317-3322, 1968.
Chonchol, M., et al., 25-Hydroxyvitamin D, insulin resistance, and kidney function in the Third National Health and Nutrition Examination Survey, Kidney Int. 71(2):134-139, 2007.
Deluca, H. F., Overview of general physiologic features and functions of vitamin D, Am. J. Clin. Nutr. 80 (suppl):1689S-16896S, 2004.
Garland, C. F., et al., Vitamin D and prevention of breast cancer: Pooled analysis, J. Steroid Biochem. and Mol. Biol. 103 (3-5 Special Issue):708-711, 2007.
Gorham, E. D., et al., Optimal Vitamin D Status for Colorectal Cancer Prevention—A Quantitative Meta Analysis, Am. J. Prev. Med. 32(3):210-216, 2007.
Graff, I. E., et al., Plasma levels of vitamin D3 metabolites during parr-smolt transformation of Atlantic salmon Salmo salar L, Aquaculture 240:617-622, 2004.
Griffing, G. T., et al., Mother Was Right About Cod Liver Oil, Medscape J. Med. 10(1):8, 2008.
Hypponen, E., et al., Intake of vitamin D and risk of type 1 diabetes: a birth-cohort study, Lancet 358:1500-1503, 2001.
Jakobsen, J., et al., 25-Hydroxyvitamin D3 affects vitamin D status similar to vitamin D3 in pigs—but the meat produced has a lower content of vitamin D, British Journal of Nutrition 98(5):908-913, 2007.
Jones, G., et al., Current Understanding of the Molecular Actions of Vitamin D, Physiol. Rev. 78:1193-1231, 1998.
Jones, G., et al., Isolation and Identification of 1,25-Dihydroxyvitamin D2, Biochemistry 14(6):1250-1256, 1975.
Li, H., et al., A Prospective Study of Plasma Vitamin D Metabolites, Vitamin D Receptor Polymorphisms, and Prostrate Cancer, Plos Medicine 4(3):562-571, 2007.
Lim, H. W., et al., Commentary: A responsible approach to maintaining adequate serum vitamin D levels, J. Am. Acad. Dermatol. 57(4):594-595, 2007.
Looker, A. C., et al., Serum 25-Hydroxyvitamin D Status of Adolescents and Adults in Two Seasonal Subpopulations from NHANES III, Bone 30(5):771-777, 2002.
Looker, A. C., et al., Serum 25-Hydroxyvitamin D and Hip Fracture Risk in Older U.S. White Adults, J. Bone Min. Res. 23(1):143-150, 2008.
Mawer, E. B., et al., The Distribution and Storage of Vitamin D and Its Metabolites in Human Tissues, Clin. Sci. 43 (3):413-431, 1972.
Munger, K. L., et al., Elevated serum 25-hydroxyvitamin D predicts a decreased risk of MS, Multiple Sclerosis 13 (2):290, 2007.
Ovesen, L., et al., Food Contents and Biological Activity of 25-Hydroxyvitamin D: a Vitamin D Metabolite to be Reckoned With?, Ann. Nutr. Metab. 47:107-113, 2003.
Purchas, R., et al., Concentrations of vitamin D3 and 25-hydroxyvitamin D3 in raw and cooked New Zealand beef and lamb, Journal of Food Composition and Analysis 20(2):90-98, 2007.
Rajakumar, K., et al., Solar Ultraviolet Radiation and Vitamin D: A Historical Perspective, Am. J. Public Health 97 (10):1746-1754, 2007.
Rosenstreich, S, et al., Deposition in and Release of Vitamin D3 from Body Fat: Evidence for a Storage Site in the Rat, J. Clin. Invest. 50(3):679-687, 1971.
Sayre, R. M., et al., Reintroduction of a classic vitamin D ultraviolet source, J. Steroid Biochem. and Molecular Biol. 103 (3-5 Special Issue):686-688, 2007.
Scientific Advisory Committee on Nutrition, Update on Vitamin D. Position Statement by the Scientific Advisory Committee on Nutrition, London: The Stationery Office, Limited, 2007.
Shepard, R. M., et al., Plasma Concentrations of Vitamin D3 and Its Metabolites in the Rat as Influenced by Vitamin D3 or 25-Hydroxyvitamin D3 Intakes, Arch. Biochem. Biophys. 202:43-53, 1980.
Sjoden, G., et al., Antirachitic Activity of 1a-Hydroxyergocalciferol and 1a-Hydroxycholecalciferol in Rats, Journal of Nutrition 114:2043-2046, 1984.
Thacher, T. D., et al., Nutritional rickets around the world: causes and future directions, Annals of Tropical Paediatrics 26(1):1-16, 2006.
European Patent Office, Extended European Search Report, Application No. 09801055.6, Nov. 3, 2011.
Ish-Shalom, et al., SU428: Daily, Weekly or Monthly Protocols to Reach the Desired Serum 25-Hydroxyvitamin D Concentration for the Elderly, Journal of Bone and Mineral Research, 27th Annual Meeting of the American Society for Bone and Mineral Research, New York, NY, vol. 20, No. 9, Suppl. 1, p. S288, Sep. 1, 2005, XP009153422, Abstract.
R.M.Shepard et al., Plasma Concentrations of Vitamin D3 and its Metabolites in the Rat as Influenced by Viatmin D3 or 25-Hydroxyvitamin D3 Intakes; Archives of Biochemistry and Biophysics, 1980, 202(1):43-53.
H.F.Deluca et al., 1,25-Dihydroxyvitamin D is not responsible for toxicity caused by vitamin D or 25-hydroxyvitamin D; Archives of Biochemistry and Biophysics, 2011, 505:226-230.
B.R.Becklund et al., Natl. Acad. Sci. USA 2010, 107:6418-6412; National Academy of Sciences.
L.Schubert and H.F.Deluca et al., Arch. Biochem. Biophys. 2010, 500:157-161.

* cited by examiner

ONCE-A-WEEK ADMINISTRATION OF 25-HYDROXY VITAMIN $D_3$ TO SUSTAIN ELEVATED STEADY-STATE PHARMACOKINETIC BLOOD CONCENTRATION

CROSS REFERENCE TO RELATED APPLICATIONS

This application claims priority from U.S. provisional application Ser. No. 61/083,223 filed Jul. 24, 2008 which is incorporated by reference in its entirety for all purposes.

STATEMENT OF GOVERNMENT INTEREST

Not applicable.

BACKGROUND OF THE INVENTION

In 1968, the 25-hydroxy-vitamin $D_3$ (25-$(OH)D_3$) molecule was discovered as the major blood form of vitamin D circulating in the body. (Blunt J W et al., 1968, 25-Hydroxycholecalciferol: A biologically active metabolite of vitamin $D_3$, *Biochemistry* 7:3317-3322).

25-$(OH)D_3$ was first patented in 1971 by DeLuca et al. (U.S. Pat. No. 3,607,888). Over the course of many years, measurement of 25-$(OH)D_3$ blood levels has been a significant commercial enterprise.

A large amount of work suggests that 25-$(OH)D_3$ blood levels are an excellent measurement of the vitamin D status of a patient who might be suffering from a metabolic bone disease. (Jones G et al., 1998, Current understanding of the molecular actions of vitamin D, *Physiol. Rev.* 78:1193-1231).

Recently, a large number of epidemiological studies correlate 25-$(OH)D_3$ blood levels to a reduced risk of a number of conditions: colorectal cancer (Gorham E D et al., 2007, Optimal vitamin D status for colorectal cancer prevention—A quantitative meta analysis, *Am. J. Prev. Med.* 32(3): 210-216); breast cancer (Garland C F et al., 2007, Vitamin D and prevention of breast cancer: Pooled analysis, *J. Steroid Biochem. and Mol. Biol.* 103:3-5 Special issue, pp. 708-711); prostate cancer (Li H J et al., 2007, A prospective study of plasma vitamin D metabolites, vitamin D receptor polymorphisms, and prostate cancer, *Plos Medicine* 4(3):562-571); and, autoimmune diseases such as multiple sclerosis and type 1 diabetes (Munger K L et al., 2007, Elevated serum 25-hydroxyvitamin D predicts a decreased risk of MS, *Multiple Sclerosis* 13(2):290; and, Hyppönen, E Läärä et al., 2001, Intake of vitamin D and risk of type 1 diabetes: a birth-cohort study, *Lancet* 358:1500-1503). Thus, 25-$(OH)D_3$ plasma levels have become a focal point of public health policy in the United States and many other countries.

25-$(OH)D_3$ is no longer available in the U.S. market. It is not available as a prescription drug nor as a vitamin supplement. However, 25-$(OH)D_3$ plasma levels are measured to assess vitamin D status.

At a 25-$(OH)D_3$ blood level concentration greater than 450 ng/ml, toxicity becomes a concern. (Shepard R M et al., 1980, Plasma Concentration of Vitamin $D_3$ and Its Metabolites in the Rat as Influenced by Vitamin $D_3$ or 25-Hydroxyvitamin $D_3$ Intakes, *Arch. Biochem. Biophys.* 202:43-53).

To promote public health, vitamin D production and administration have focused on exposure to ultraviolet light. (Sayre R M et al., 2007, Reintroduction of a classic vitamin D ultraviolet source, *J. Steroid Biochem. and Molecular Biol.* 103(3-5 Special Issue):686-688; and, Rajakumar K et al., 2007, Solar ultraviolet radiation and vitamin D: A historical perspective, *Am. J. Public Health* 97(10):1746-1754).

Dermatologists are not in favor of using skin production of vitamin D to meet increased blood level concentrations. Small amounts of ultraviolet light exposure markedly increases the risk of melanoma, basal cell carcinoma, and squamous cell carcinoma of the skin. (Lim H W et al., 2007, Commentary: A responsible approach to maintaining adequate serum vitamin D levels, *J. Am. Acad. Dermatology* 57(4):594-595).

Currently, the only forms of vitamin D available in the U.S. are vitamin $D_3$ and vitamin $D_2$, which are present in cod liver oil. However, cod liver oil contains significant amounts of other biopotent materials such as vitamin A. (Griffing G T et al., 2008, Mother was right about cod liver oil, *Medscape J. Med.* 10(1):8).

It has been reported that the conversion of vitamin $D_3$ to 25-$(OH)D_3$ in vivo is not quantitative. (Heaney R P et al., 2008, 25-Hydroxylation of vitamin $D_3$: relation to circulating vitamin $D_3$ under various input conditions, *Am. J. Clin. Nutr.* 87(6):1738-1744).

Upon administration of vitamin $D_3$ or vitamin $D_2$, often, a significant amount of it is deposited in lipid depots, and, vitamins $D_3$ and $D_2$ remain there until the lipid is mobilized. (Mauer E B et al., 1972, Distribution and storage of vitamin-D and its metabolites in human tissues. Clin. Sci. 43(3):413-431 (1972); Rosenstreich et al., 1971, Deposition in and release of vitamin $D_3$ from body fat: Evidence for a storage site in the rat, *J. Clin. Invest.* 50(3):679-687).

Continued vitamin $D_3$ supplementation intake causes increased concentrations levels in the adipose tissue, which eventually reaches saturation and forces elevated conversion to 25-$(OH)D_3$. Such conversion, however, causes vitamin D intoxication, which is difficult to resolve.

Deficiency or insufficiency of vitamin D exists in the human population, which has been extensively reported in the clinical literature. (Looker A C et al., 2002, Serum 25-hydroxyvitamin D status of adolescent and adults in two seasonal subpopulations from NHANES III, *Bone* 30(5):771-777).

An increased incidence of childhood rickets and osteomalacia has been reported to exist in the inner cities and in dark skinned immigrants living in the Northern hemispheres. (Thacher T D et al., 2006, Nutritional rickets around the world: causes and future directions, *Annals of Tropical Paediatrics* 26(1):1-16).

Some commentators have theorized that vitamin D insufficiency contributes to the bone erosion process, i.e., osteoporosis. (Looker A C et al., 2008, Serum 25-hydroxyvitamin D and hip fracture risk in older U.S. white adults, *J. Bone Min. Res.* 23(1):143-150).

In patients suffering from chronic kidney disease, there is evidence of vitamin D insufficiency that may contribute to continued disease progression (Chonchol M et al., 2007, 25-Hydroxyvitamin D, insulin resistance, and kidney function in the Third National Health and Nutrition Examination Survey, *Kidney Int.* 71(2):134-139). Hence, there exists a long-felt and important unmet need for maintaining higher blood levels of 25-$(OH)D_3$.

SUMMARY OF THE INVENTION

One aspect of the invention is an oral dosage form comprising a single dose of 25-hydroxy-vitamin $D_3$, or the monohydrate thereof, sufficient to sustain the serum level in a human in need thereof to a concentration in the range of 30 ng/ml to 200 ng/ml for at least 7 days at steady-state pharmacokinetics, and a pharmaceutically suitable oral carrier system.

In an exemplary embodiment of the oral dosage form, each single dose administered weekly is sufficient to sustain the serum level in the human to a concentration in the range of 30 ng/ml to 200 ng/ml at steady-state pharmacokinetics.

In another exemplary embodiment of the oral dosage form, the concentration is in the range of 30 ng/ml to 100 ng/ml.

In another exemplary embodiment of the oral dosage form, the oral dosage form is a soft gel capsule.

In another exemplary embodiment of the oral dosage form, the pharmaceutically suitable carrier system comprises one or more digestible oils.

In another exemplary embodiment of the oral dosage form, the oral dosage form is a tablet.

In another exemplary embodiment of the oral dosage form, the single weekly dose is in the range of 10-100 μg/kg body weight, preferably 30-50 μg/kg body weight of 25-hydroxy-vitamin $D_3$ or the monohydrate thereof.

In another exemplary embodiment of the oral dosage form, the single weekly dose is in the range of 0.6 mg-6 mg of 25-hydroxy-vitamin $D_3$ or the monohydrate thereof.

Another aspect of the invention is a parenteral dosage form comprising a single dose of 25-hydroxy-vitamin $D_3$, or the monohydrate thereof, sufficient to sustain the serum level in a human in need thereof to a concentration in the range of 30 ng/ml to 200 ng/ml for at least 7 days at steady-state pharmacokinetics, and, a pharmaceutically suitable parenteral carrier system, wherein the parenteral dosage form is an injectable dosage form or an infusion dosage form.

In an exemplary embodiment of the parenteral dosage form, each single dose is administered weekly and is sufficient to sustain the serum level in the human to a concentration in the range of 30 ng/ml to 200 ng/ml at steady-state pharmacokinetics.

In another exemplary embodiment of the parenteral dosage form, the concentration is in the range of 30 ng/ml to 100 ng/ml.

In another exemplary embodiment of the parenteral dosage form, the single weekly dose is in the range of 10-100 μg/kg body weight, preferably 30-50 μg/kg body weight of 25-hydroxy-vitamin $D_3$ or the monohydrate thereof.

In another exemplary embodiment of the parenteral dosage form, the single dose is in the range of 0.6 mg-6 mg of 25-hydroxy-vitamin $D_3$ or the monohydrate thereof.

Another aspect of the invention is a method of sustaining the blood level concentration of 25-hydroxy-vitamin $D_3$ at steady-state pharmacokinetics in a human in need thereof comprising orally administering, at least once every 7 days, a single dose of 25-hydroxy-vitamin $D_3$, or the monohydrate thereof, sufficient to sustain the serum level in a human to a concentration in the range of 30 ng/ml to 200 ng/ml for at least 7 days at steady-state pharmacokinetics.

In an exemplary embodiment of method, each single dose is administered weekly and is sufficient to sustain the serum level in the human to a concentration in the range of 30 ng/ml to 200 ng/ml at steady-state pharmacokinetics.

In another exemplary embodiment of the method, the concentration is in the range of 30 ng/ml to 100 ng/ml.

In another exemplary embodiment of the method, the single dose is in the range of 10-100 μg/kg body weight, preferably 30-50 μ/kg body weight of 25-hydroxy-vitamin $D_3$ or the monohydrate thereof.

In another exemplary embodiment of the method, the single dose is in the form of a soft gel capsule or a tablet.

In another exemplary embodiment of the method, the human in need thereof is a human deficient in vitamin D having a serum level concentration of 25-hydroxy-vitamin $D_3$ less than 30 ng/ml.

In another exemplary embodiment of the method, the human in need thereof is a human deficient in vitamin D having a serum level concentration of 25-hydroxy-vitamin $D_3$ in the range of 10 ng/ml to 20 ng/ml.

Another aspect of the invention is a method of sustaining the blood level concentration of 25-hydroxy-vitamin $D_3$ at steady-state pharmacokinetics in a human in need thereof comprising parenterally administering by injection or infusion, at least once every 7 days, a single dose of 25-hydroxy-vitamin $D_3$, or the monohydrate thereof, sufficient to sustain the serum level in the human to a concentration in the range of 30 ng/ml to 200 ng/ml for at least 7 days at steady-state pharmacokinetics.

In an exemplary embodiment of the method, each single dose is administered weekly and is sufficient to sustain the serum level in the human to a concentration in the range of 30 ng/ml to 200 ng/ml at steady-state pharmacokinetics.

In another exemplary embodiment of the method, the concentration is in the range of 30 ng/ml to 100 ng/ml.

In another exemplary embodiment of the method, the single dose is in the range of 10-100 μg/kg body weight, preferably 30-50 μg/kg body weight of 25-hydroxy-vitamin $D_3$ or the monohydrate thereof.

In another exemplary embodiment of the method, the single dose is in the range of 0.6 mg-6 mg of 25-hydroxy-vitamin $D_3$ or the monohydrate thereof.

In another exemplary embodiment of the method, the human in need thereof is deficient in vitamin D having a serum level concentration of 25-hydroxy-vitamin $D_3$ less than 30 ng/ml.

In another exemplary embodiment of the method, the human in need thereof is deficient in vitamin D having a serum level concentration of 25-hydroxy-vitamin $D_3$ in the range of 10 ng/ml to 20 ng/ml.

Another aspect of the invention is a method of sustaining the blood level concentration of 25-hydroxy-vitamin $D_3$ at steady-state pharmacokinetics in a human in need thereof comprising transdermally administering, at least once every 7 days, a single dose of 25-hydroxy-vitamin $D_3$, or the monohydrate thereof, in a transdermal dosage form, sufficient to sustain the serum level in the human to a concentration in the range of 30 ng/ml to 200 ng/ml for at least 7 days at steady-state pharmacokinetics.

Another aspect of the invention is a method of sustaining the blood level concentration of 25-hydroxy-vitamin $D_3$ at steady-state pharmacokinetics in a human in need thereof comprising administering by inhalation, at least once every 7 days, a single dose of 25-hydroxy-vitamin $D_3$, or the monohydrate thereof, in an inhalation dosage form, sufficient to sustain the serum level in the human to a concentration in the range of 30 ng/ml to 200 ng/ml for at least 7 days at steady-state pharmacokinetics.

One aspect of the invention is a dosage form comprising a single dose of 25-hydroxy-vitamin $D_2$, or the monohydrate thereof, sufficient to sustain the serum level in a human in need thereof to a concentration in the range of 30 ng/ml to 200 ng/ml for at least 7 days at steady-state pharmacokinetics, and a pharmaceutically suitable carrier system. The concentration and dose of 25-hydroxy-vitamin $D_2$ (25-$(OH)D_2$) would be similar to that of 25-hydroxy-vitamin $D_3$ (25-$(OH)D_3$).

BRIEF DESCRIPTION OF DRAWINGS OF THE EXEMPLARY EMBODIMENTS

Figure 9:
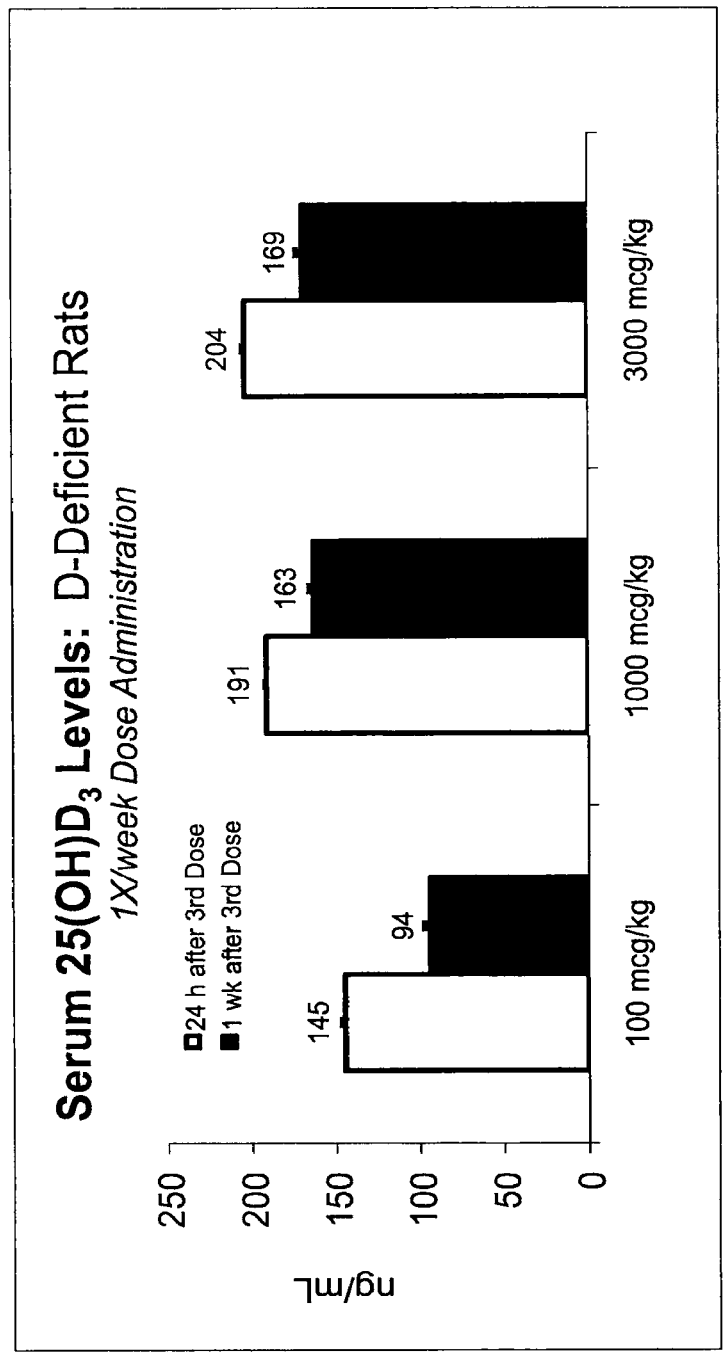

FIG. 9 is a bar graph showing increased 25-(OH)$D_3$ levels after 1× weekly dosing with 25(OH)$D_3$.

Figure 10:
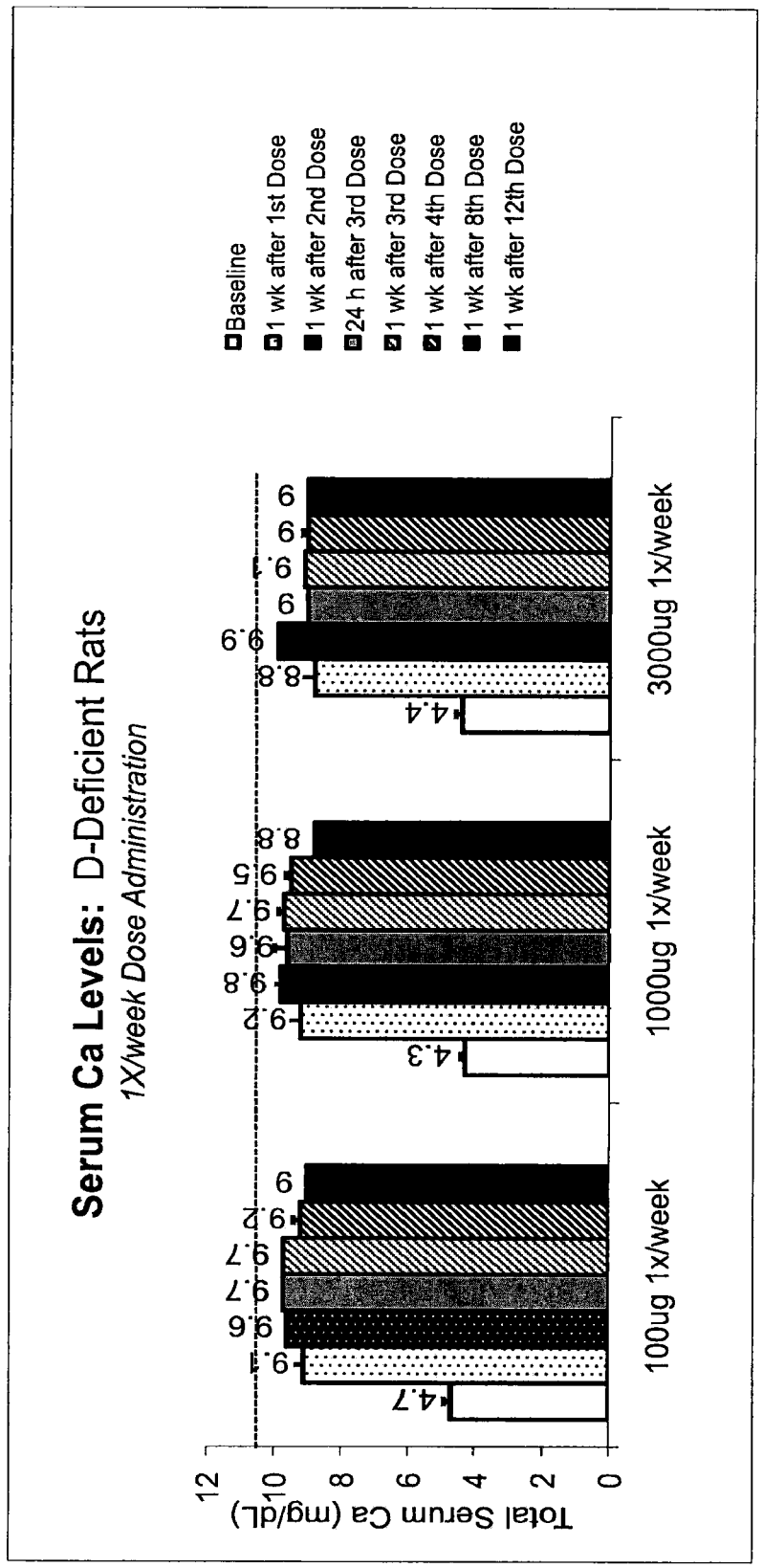

FIG. 10 is a bar graph exhibiting no increases of serum Ca concentrations above the normal range (dotted) line after 1× weekly dosing.

DETAILED DESCRIPTION OF THE EXEMPLARY EMBODIMENTS

The active ingredient of the instant invention is 25-hydroxy-vitamin $D_3$, which is also referred to as calcifediol and 25-hydroxy-cholecalciferol. It is also referred to as (5Z,7E)-9,10-secocholesta-5,7,10(19)-triene-3β,25 diolmonohydrate. 25-hydroxy-vitamin $D_3$ is still further referred to as 25-HCC and 25-OHCC. The active ingredient may be an active pharmaceutical ingredient (API), a supplement ingredient, or a nutritional ingredient. The structure of 25-(OH)$D_3$ is shown below.

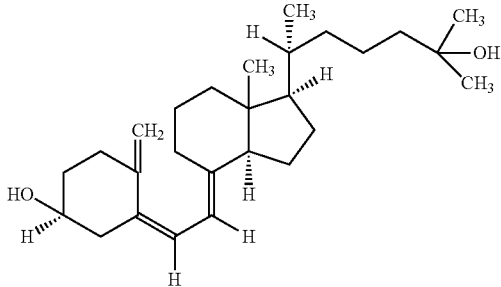 [SMILES: C=C1CC[C@H](O)C/C1=C/C=C1\CCCC2(C)[C@@H]([C@H](C)CCCC(C)(C)O)CC[C@@H]12]

25-(OH)$D_3$ is soluble in organic solvents and relatively insoluble in water. 25-(OH)$D_3$ can exist in its free form or as a monohydrate. 25-(OH)$D_3$ monohydrate is crystalline.

25-(OH)$D_3$ was originally introduced into the U.S. Pharmacopeia as a drug called CALDEROL® for treating renal osteodystrophy. CALDEROL® is no longer available in the U.S. In France, 25-(OH)$D_3$ is the active pharmaceutical ingredient in DEDROGYL®. Apparently, DEDROGYL® is used to treat spasmophilia.

Clinical Pharmacology of 25-(OH)$D_3$. The natural supply of vitamin D in humans mainly depends on the ultraviolet rays of the sun for conversion of 7-dehydrocholesterol to vitamin $D_3$ (cholecalciferol). Vitamin $D_3$ is converted to 25-(OH)$D_3$ by the vitamin $D_3$-hydroxylase enzyme (25-OHase) present in the liver. 25-hydroxycholecalciferol is the major transport form of vitamin $D_3$ and can be readily monitored in the serum. It is further converted to 1,25-dihydroxycholecalciferol (1,25-(OH)$_2D_3$) and 24,25-dihydroxy-cholecalciferol (24,25-(OH)$_2D_3$) in the kidney. 1,25-(OH)$_2D_3$ stimulates resorption of calcium from bone and increases intestinal calcium absorption. The metabolic activity of calcifediol in clinical use appears to be related not only to its conversion to other metabolites but also to its intrinsic activity. When administered orally, 25-(OH)$D_3$ is rapidly absorbed from the intestine with peak 25-(OH)$D_3$ concentrations in the serum reported after about 4 hours. 25-(OH)$D_3$ is known to be transported in blood, bound to a specific plasma protein. (Package Insert, Calderol®, Calcifediol Capsules, USP, September 1998). The half-life of orally administered 25-(OH)$D_3$ is in the range of 12-23 days. When orally administered, around 62-77% of the 25-(OH)$D_3$ is absorbed in man. The physiology of vitamin D has also been reported in DeLuca H F, 2004, Overview of general physiologic features and functions of vitamin $D^{1-4}$, Am J Clin Nutr 80(suppl):1689S-16896S, which is incorporated herein by reference.

The instant invention is directed to a logical approach to 25-(OH)$D_3$ supplementation, which is the form of vitamin D present in blood. There is no reported evidence that 25-(OH)$D_3$ is stored in the form of a depot in the body, so supplementation can be advantageously used to titer blood level concentrations. The instant invention contemplates a prescription vitamin capsule containing 25-(OH)$D_3$ that, when administered, will improve public health.

25-(OH)$D_3$ has a lifetime in the body of approximately 25-32 days. (Summary Basis of Approval for Calderol, 25-(OH)$D_3$). Thus, no controlled release dosage form is needed to administer 25-(OH)$D_3$ in a once-per-month dosing regimen, such as oral and parenteral by injection or infusion. The lifetime of 25-(OH)$D_3$ can, however, be used advantageously in terms of frequency of dosing.

The once-a-week oral and parenteral dosage forms of the instant invention maintain blood levels of 25-(OH)$D_3$ between 30 ng/ml and 100 ng/ml throughout the month. The instant dosage form also treats frank deficiency, which represents blood levels of 25-(OH)$D_3$ below 30 ng/ml, usually between 10-20 ng/ml. (Scientific Advisory Committee on Nutrition Update on Vitamin D. Position Statement by the Scientific Advisory Committee on Nutrition, London: The Stationery Office, Limited, 2007).

25-(OH)$D_3$ is readily absorbed and bioavailable from oils or from capsules. Capsules containing up to 50 mg of 25-(OH)$D_3$ may be used for a once-a-week dosing regimen. The instant experimentals in rats show that 100 μg/$kg_{BW}$ is sufficient to maintain blood levels in the range of 30 ng/ml to 100 ng/ml. The instant invention does not contemplate dosage forms or dosing regimens that would raise 25-(OH)$D_3$ levels above 500 ng/ml because that would run the risk of causing a mild vitamin D intoxication. (Shepard R M et al., 1980, Plasma Concentration of Vitamin $D_3$ and Its Metabolites in the Rat as Influenced by Vitamin $D_3$ or 25-Hydroxyvitamin $D_3$ Intakes, *Arch Biochem Biophys* 202:43-53).

25-$(OH)D_3$ is also a normal food constituent, or nutritional. It is found in blood and tissues of animals that are consumed for food. (Purchas R et al., 2007, Concentrations of vitamin $D_3$ and 25-hydroxyvitamin $D_3$ in raw and cooked New Zealand beef and lab, *Journal of food Composition and Analysis* 20(2):90-98); Jakobsen J et al., 2007, 25-Hydroxyvitamin D-3 affects vitamin D status similar to vitamin D-3 in pigs—but the meat produced has a lower content of vitamin D, *British Journal of Nutrition* 98(5):908-913); Graff I E et al., 2004, Plasma levels of vitamin $D_3$ metabolites during parr-smolt transformation of Atlantic salmon Salmo salar L, *Aquaculture* 240:617-622); and, Ovesen L C et al., Food contents and biological activity of 25-hydroxyvitamin D: a vitamin D metabolite to be reckoned with? *Annals of Nutrition and Metabolism* 47(3-4):107-113).

25-$(OH)D_3$ can be found in the GRAS list for avian feeds. Hence, it is accepted as a normal nutrient. 25-$(OH)D_3$ is structurally close to the active form of vitamin D, however, it still requires conversion to $1\alpha,25$-dihydroxyvitamin $D_3$, $1,25$ $(OH)_2D_3$. Such conversion is a controlled process occurring in the kidney. 25-Hydroxyvitamin $D_3$ advantageously possesses the current nutritional forms. It can also be advantageously, conveniently, and routinely measured.

Human Dosage Forms. The envisioned human dose is 10-100 μg/kg body weight, preferably 30-50 μg/kg body weight. Based upon the rat dosage forms and data, a 60 kg human deficient or insufficient in vitamin D can be safely dosed with 1-10 mg of 25-$(OH)D_3$ once a month, which would raise blood circulating concentration levels of 25-$(OH)D_3$ above the normal range. Such dosing of 25-$(OH)D_3$ also sustains an elevation in blood concentrations of 25-OH-$D_3$, particularly upon reaching steady-state pharmacokinetics. At steady-state pharmacokinetics, the maintenance dose of 25-$(OH)D_3$ is equal to the rate of elimination of 25-$(OH)D_3$ from the body. In other words, the rate of administration is equal to the rate of elimination. Steady-state serum concentration is also referred to in terms of mean steady-state serum concentration. Prior to dosing the subject with the 25-$(OH)D_3$, the subject has an innate steady-state baseline serum concentration of 25-$(OH)D_3$.

In an exemplary embodiment, the oral dosage form is a capsule containing 0.6 mg to 6 mg of 25-$(OH)D_3$. The capsule may be in a variety of forms. For example, it may be a soft gel capsule containing the 25-$(OH)D_3$ in 0.1 ml to 1 ml of a digestible oil. The dosage form may also be a tablet containing a carrier system that includes one or more suitable pharmaceutical excipients.

The pharmaceutically suitable oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, the oral dosage form includes capsules (a solid oral dosage form consisting of a shell and a filling, whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle), granule (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, e.g., citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), osmotic, and the like.

The oral dosage form composition contains an active pharmaceutical ingredient (i.e., the 25-hydroxy-vitamin $D_3$) and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the injectable and infusion dosage forms include, but are not limited to, a liposomal injectable, which either consists of or forms liposomes (a lipid bilayer vesicle usually composed of phospholipids which is used to encapsulate an active drug substance); an injection, which includes a sterile preparation intended for parenteral use; five distinct classes of injections exist as defined by the USP; an emulsion injection, which includes an emulsion consisting of a sterile, pyrogen-free preparation intended to be administered parenterally; a lipid complex injection; a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures; this is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug substances dissolved in a suitable solvent or mixture of mutually miscible solvents that is suitable for injection; a solution concentrate injection being a sterile preparation for parenteral use which, upon the addition of suitable solvents, yields a solution conforming in all respects to the requirements for injections; a suspension injection being a liquid preparation, suitable for injection, which consists of solid particles dispersed throughout a liquid phase in which the particles are not soluble that can also consist of an oil phase dispersed throughout an aqueous phase, or vice-versa; a suspension liposomal injection being a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed; a suspension sonicated injection being a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols); foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

As used herein, transdermal dosage form includes, but is not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and, other various types of transdermal patches such as matrix, reservoir and others known in the art.

In another embodiment of the present invention, one may wish to substitute 25-(OH)D$_2$ for the 25-(OH)D$_3$ described above. Dosage and concentration ranges suitable for 25(OH)D$_2$ treatment would be similar to those discussed above. Since 1,25(OH)2D$_3$ and 1,25(OH)2D$_2$ (Jones et al. 1975 Isolation and Identification of 1,25-dihydroxyvitamin D$_2$; Biochemistry 14(6):1250.) and 1a(OH)D$_3$ and 1a(OH)D$_2$ (Sjoden, Lindgren, and DeLuca, 1984 Antirachitic activity of 1α-hydroxyergocalciferol and 1α-hydroxycholecalciferol in rats Journal of Nutrition 114:2043.) have similar biopiotencies, it is likely that 25(OH)D$_2$ could be substituted for 25(OH)D$_3$ to elicit the same desired changes in circulating levels of 25(OH)D without any safety concerns.

EXAMPLES

Applicants examined the effect of once a month and once a week dosing of 25 hydroxy vitamin D$_3$ (25-(OH)D$_3$) in a rat model and have concluded that once a week dosing with 25-(OH)D$_3$ at a level of between 10-100 µg/kg of body weight is an appropriate and effective therapy for maintaining a elevated steady state blood concentration of 25-(OH)D$_3$.

Figure 1:
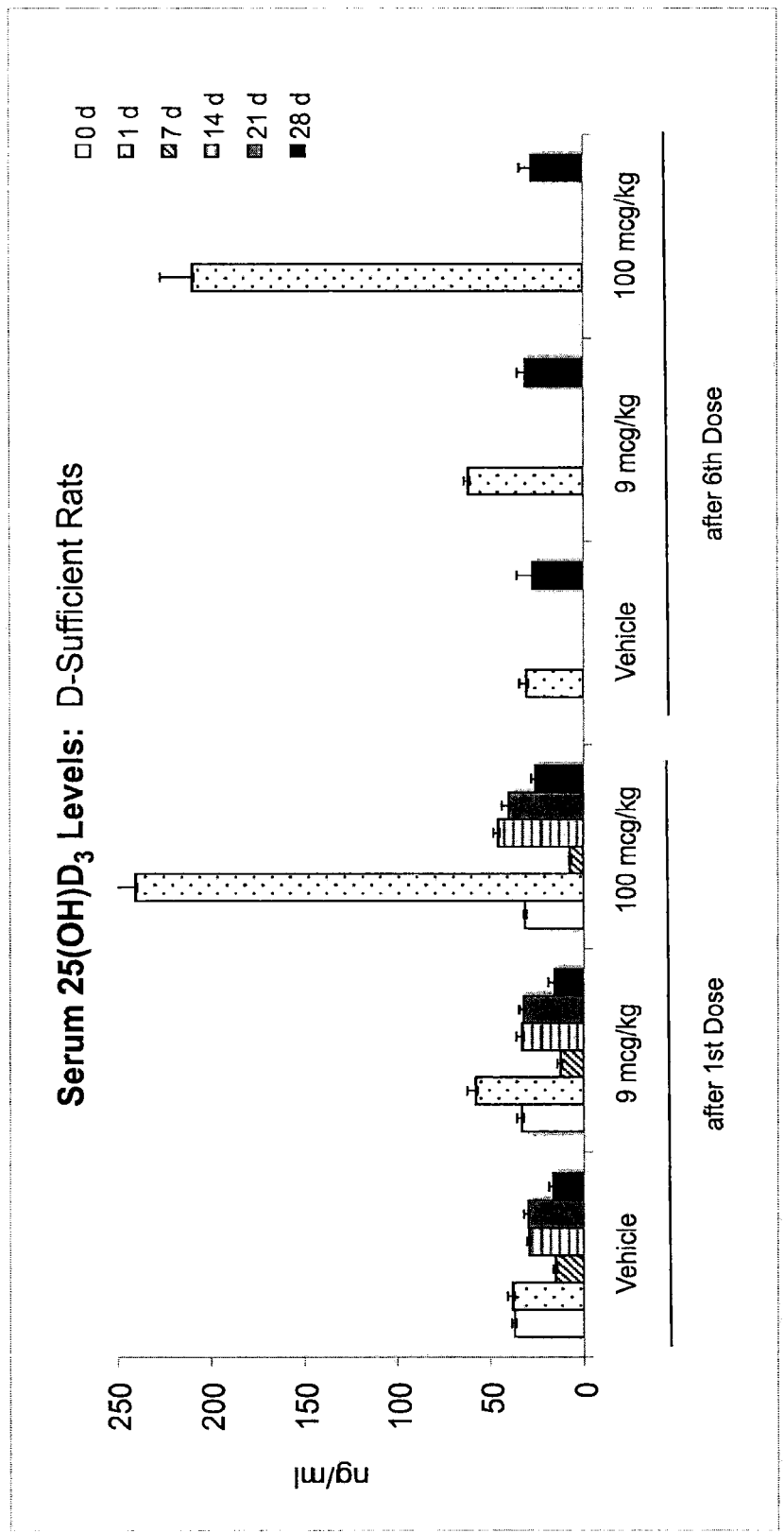
FIG. 1 is a bar graph showing exemplary elevations of serum 25-(OH)$D_3$ levels occurring after 1×/month oral administration of 25-(OH)$D_3$.

FIG. 1 is a bar graph showing exemplary elevations of serum 25-(OH)D$_3$ levels occurring after 1×/month oral administration of 25-(OH)D$_3$ at 9 and 100 mcg/kg$_{BW}$ in rats with normal vitamin D status. The rats were male, Sprague-Dawley rats (9 weeks of age, n=15) received from a commercial supplier, and the animals were placed on a purified diet containing 0.47% calcium and allowed to acclimate for one week. After one week the animals were randomly assigned to 3 groups, bled (0 d), and then orally dosed 1× every 28 days with vehicle (5% ethanol in Neobee oil) or 25-(OH)D$_3$ dissolved in ethanol and Neobee oil. Blood was again collected 4 hr, 24 hr, and 1, 2, 3 and 4 weeks after each single, oral dose was administered, and, serum 25-(OH)D$_3$ concentrations were assessed using a commercially available RIA kit (DiaSorin of Stillwater, Minn.). FIG. 1 also contains data taken after 6 months of dosing. FIG. 1 demonstrates that more frequent dosing is required because values return to baseline 4 weeks after the dose is administered.

Figure 2:
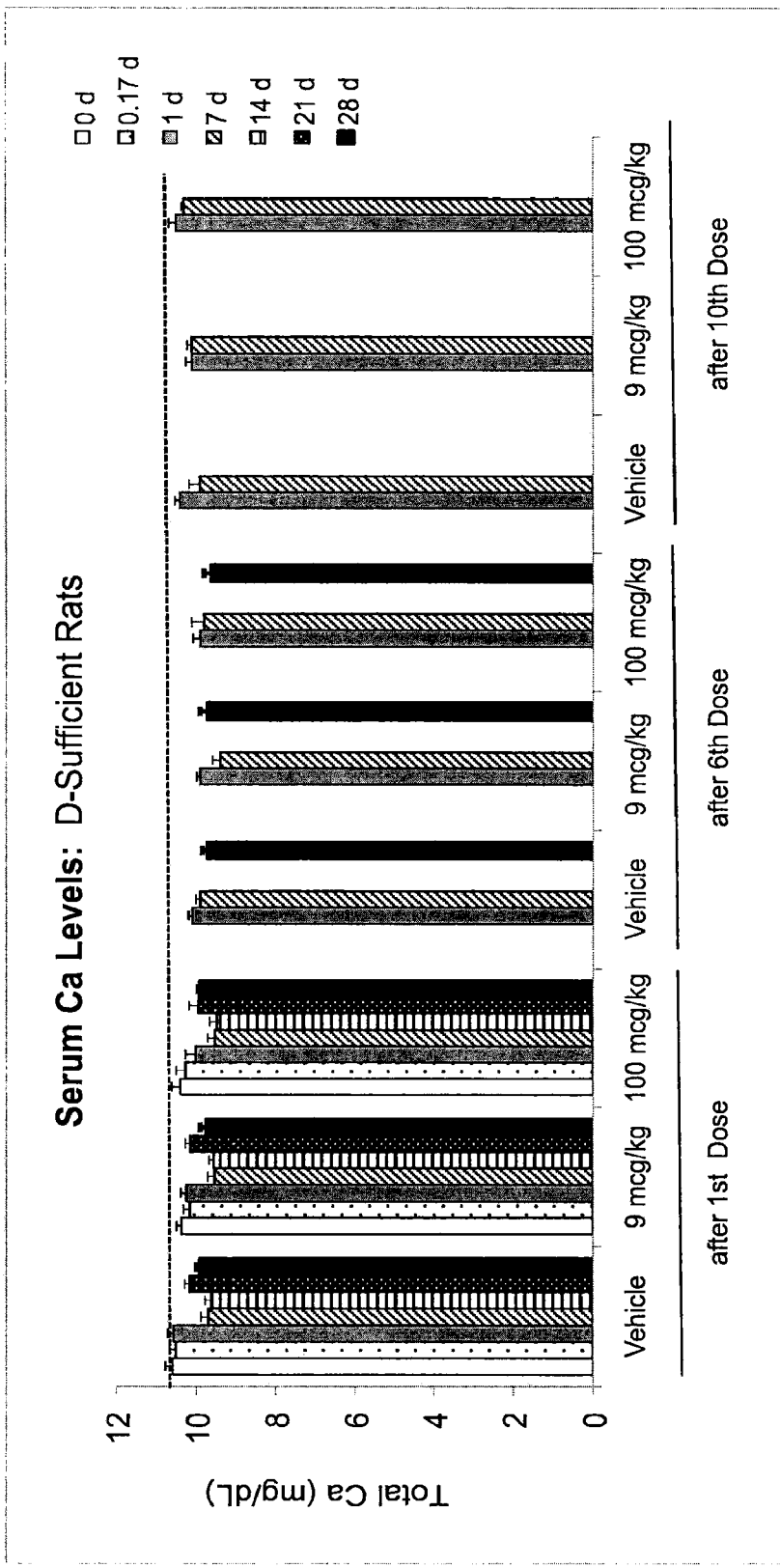
FIG. 2 is a bar graph showing no increase in serum calcium above normal levels (dotted line) occurring after 1×/month oral administration of 25-(OH)D3 in rats with normal vitamin D status.

FIG. 2 is a bar graph showing no change in serum calcium occurring after DC/month oral administration of 25-(OH)D$_3$ in rats with normal vitamin D status. The rats were male, Sprague-Dawley rats (9 weeks of age, n=15) received from a commercial supplier. The animals were placed on a purified diet containing 0.47% calcium and allowed to acclimate for one week. After one week the animals were randomly assigned to 3 groups, bled (0 d), and then orally dosed 1× every 7 days with vehicle (5% ethanol in Neobee oil) or 25-(OH)D$_3$ dissolved in ethanol and Neobee oil. Blood was again collected 4 hr, 24 h, and 1, 2, 3 and 4 weeks after each single, oral dose was administered, and total calcium concentrations were assessed in the serum using atomic absorption spectrometry. FIG. 2 also contains data taken after the 6th and 10th monthly dose. FIG. 2 demonstrates that demonstrates that the dose levels used in this study for up to 10 months do not cause hypercalcemia and that administration of higher dose levels are possible.

Figure 3:
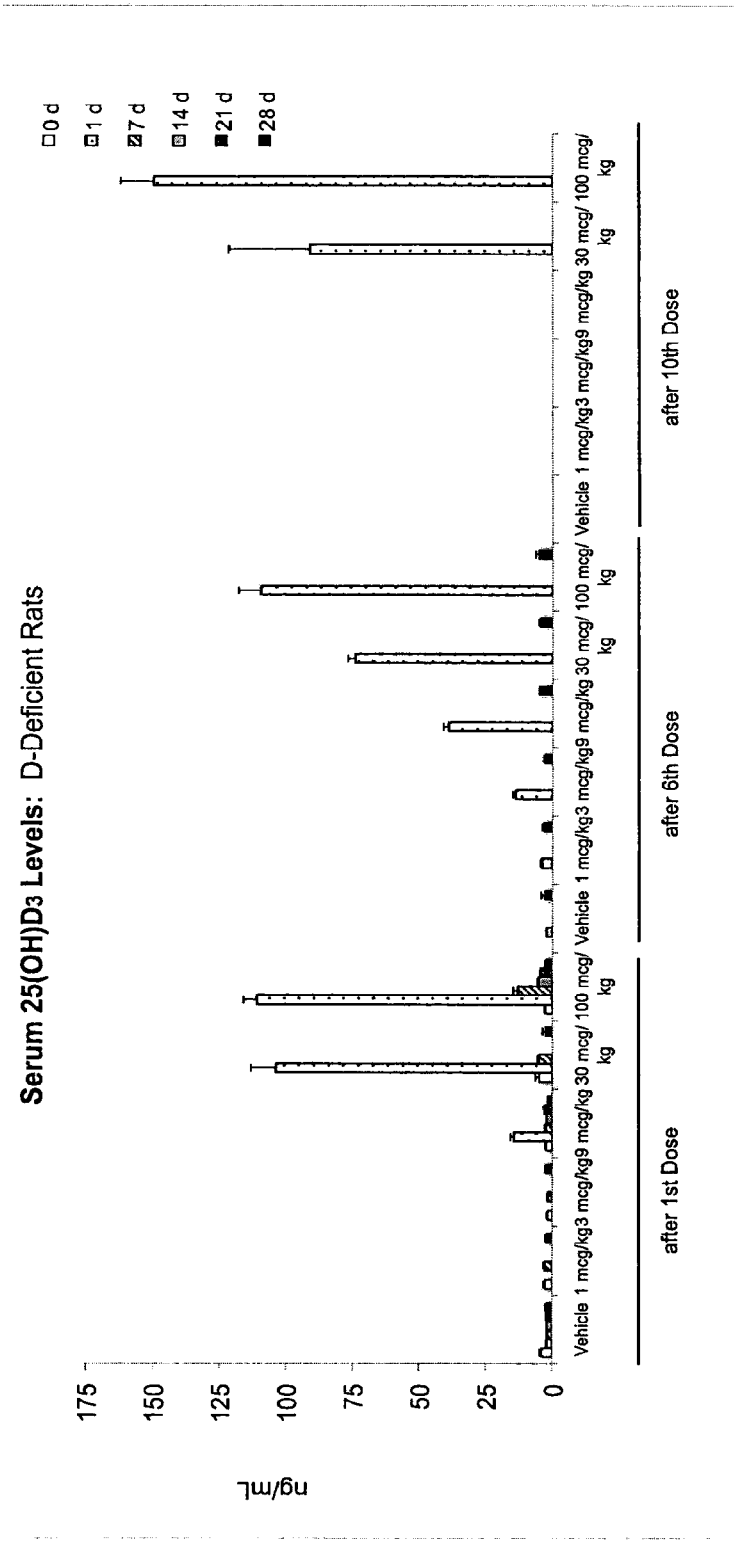
FIG. 3 is a bar graph showing exemplary elevations of serum 25-(OH)$D_3$ levels occurring after 1×/month oral administration of 25-(OH)$D_3$.

FIG. 3 is a bar graph showing exemplary elevations of serum 25-(OH)D$_3$ levels occurring after 1×/month oral administration of 25-(OH)D$_3$ at 1, 3, 9, 30 and 100 mcg/kg$_{BW}$ in vitamin D deficient rats. The rats were male, Sprague-Dawley rats (weanlings, n=30) received from a commercial supplier. The animals were placed in rooms that lacked light emissions in the UV range and were fed diets lacking any vitamin D, whereby at 10 weeks of age the animals were randomly assigned to 6 groups (n=5/group), bled (0 d), and then orally dosed 1× every 28 days with vehicle (5% ethanol in Neobee oil) or 25-(OH)D$_3$ dissolved in ethanol and Neobee oil. Blood was again collected 4 hr, 24 hr, and 1, 2, 3 and 4 weeks after each single, oral dose was administered, and serum 25-(OH)D$_3$ concentrations were assessed using a commercially available RIA kit (DiaSorin of Stillwater, Minn.). FIG. 3 includes data taken after the 6th and 10th monthly dose. FIG. 3 indicates that indicates that more frequent dosing is required in vitamin D-deficient animals because values return to baseline 4 weeks after the dose is administered.

Figure 4:
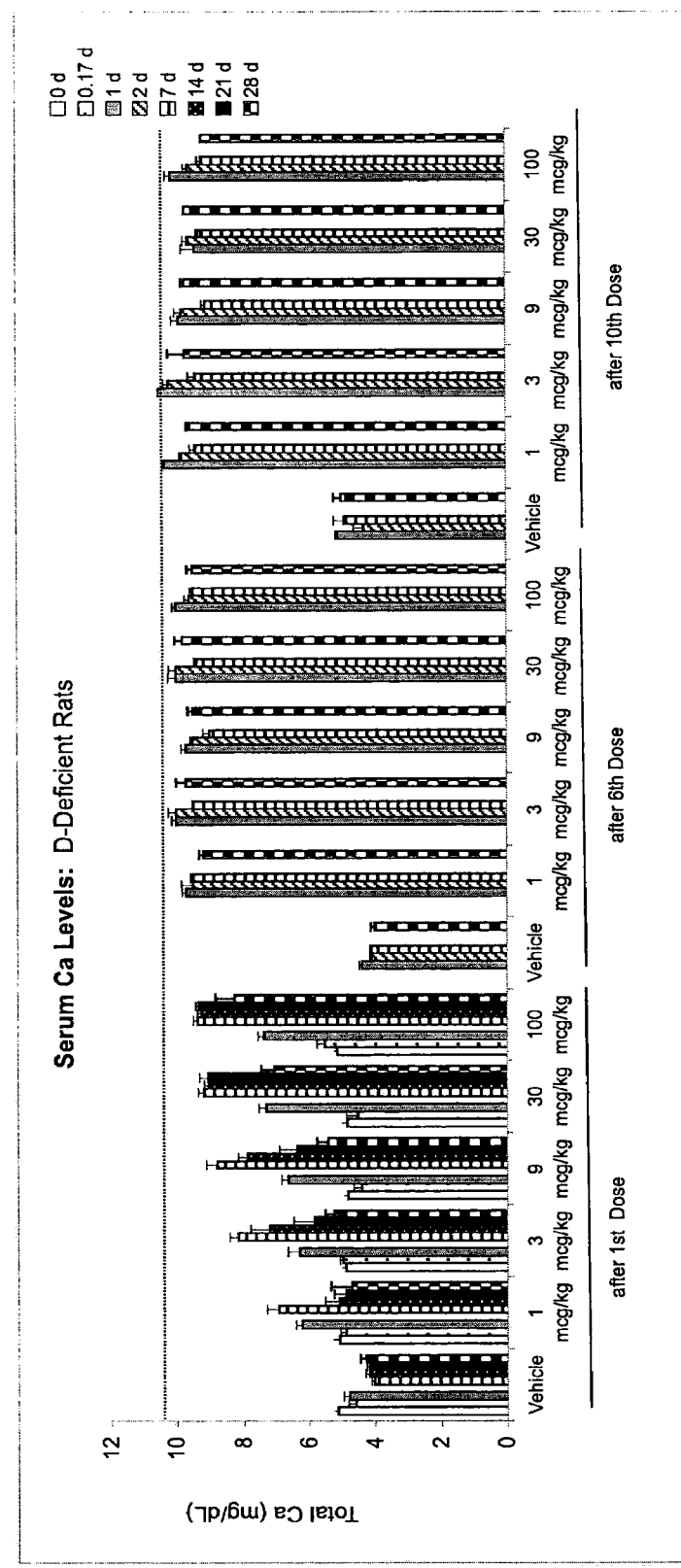
FIG. 4 is a bar graph showing no increase in serum Ca concentration levels above the normal range occurring after exemplary 1×/month oral administration of 25-(OH)$D_3$ in vitamin D-deficient rats.

FIG. 4 is a bar graph showing no increase in serum Ca concentration levels above the normal range occurring after exemplary 1×/month oral administration of 25-(OH)D$_3$ in vitamin D-deficient rats. The rats were male, Sprague-Dawley rats (weanlings, n=30) received from a commercial supplier. The animals were placed in rooms that lacked light emissions in the UV range and fed diets lacking vitamin D. At 10 weeks of age, the rats were randomly assigned to 6 groups (n=5/group), bled (0 d) and then orally dosed 1× every 28 days with vehicle (5% ethanol in Neobee oil) or 25-(OH)D$_3$ dissolved in ethanol and Neobee oil, whereby blood was again collected 4 hr, 24 hr, and 1, 2, 3 and 4 weeks after each single, oral dose was administered. Total calcium concentrations were assessed in the serum using absorption spectrometry. FIG. 4 includes data out to 10 months of dosing. FIG. 4 indicates that indicates that the dose levels used in this study for up to 10 months do not cause hypercalcemia and that administration of higher dose levels are possible.

Based on the study results shown in FIGS. 1-4, another set of studies was conducted to ascertain whether higher dose levels given 1×/monthly or similar or higher dose levels given more frequently (1×/weekly) would result in circulating blood levels of 25(OH)D$_3$ that were sustained above 30 ng/ml without increasing serum calcium outside the normal range. FIGS. 5-8 show that higher doses of 25(OH)D$_3$ given 1×/monthly to either vitamin D sufficient or vitamin D deficient animals does result in sustained elevations of 25(OH)D$_3$ in the serum without causing increases in serum calcium outside the normal range (dotted line in FIGS. 6 and 8). More frequent (1×/weekly) administration of 25(OH)D$_3$ at a lower dose results in increased blood levels of 25(OH)D$_3$ without changing serum calcium (FIGS. 9 and 10). Because 1×/weekly administration of 25(OH)D$_3$ results in less severe changes in 25(OH)D$_3$ concentrations, and lower amounts can be used and still sustain desired levels, it could be the more desirable dosing regimen.

Figure 5:
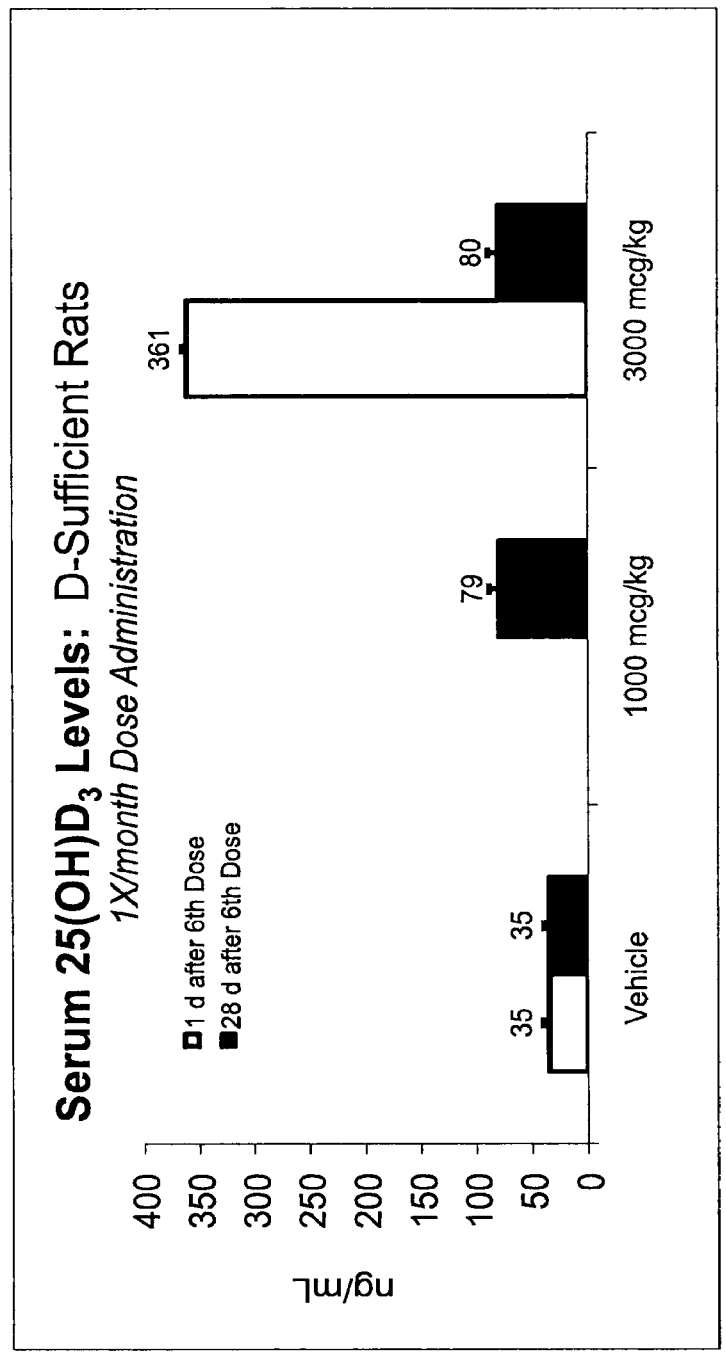
FIG. 5 is a bar graph showing that higher doses of 25(OH)$D_3$ given to D-sufficient rats results in circulating levels higher than normal.

FIG. 5 is a bar graph illustrating the increases in serum 25(OH)D$_3$ occurring after 1×/monthly oral administration of 25(OH)D$_3$ at 1000 and 3000 mcg/kg body weight in rats with normal vitamin D status. The rats were male, Sprague-Dawley rats (9 weeks of age, n=4-6 animals/group) received from a commercial supplier. The animals were placed on a purified diet containing 0.47% calcium and allowed to acclimate for one week, whereby after one week the animals were randomly assigned to 3 groups, and then orally dosed 1× every 28 days with vehicle (5% ethanol in Neobee oil) or 25(OH)D$_3$ dissolved in ethanol and Neobee oil. Blood was collected at the times indicated in the graph, and serum 25(OH)D$_3$ concentrations were assessed using a commercially available RIA kit (DiaSorin of Stillwater, Minn.).

Figure 6:
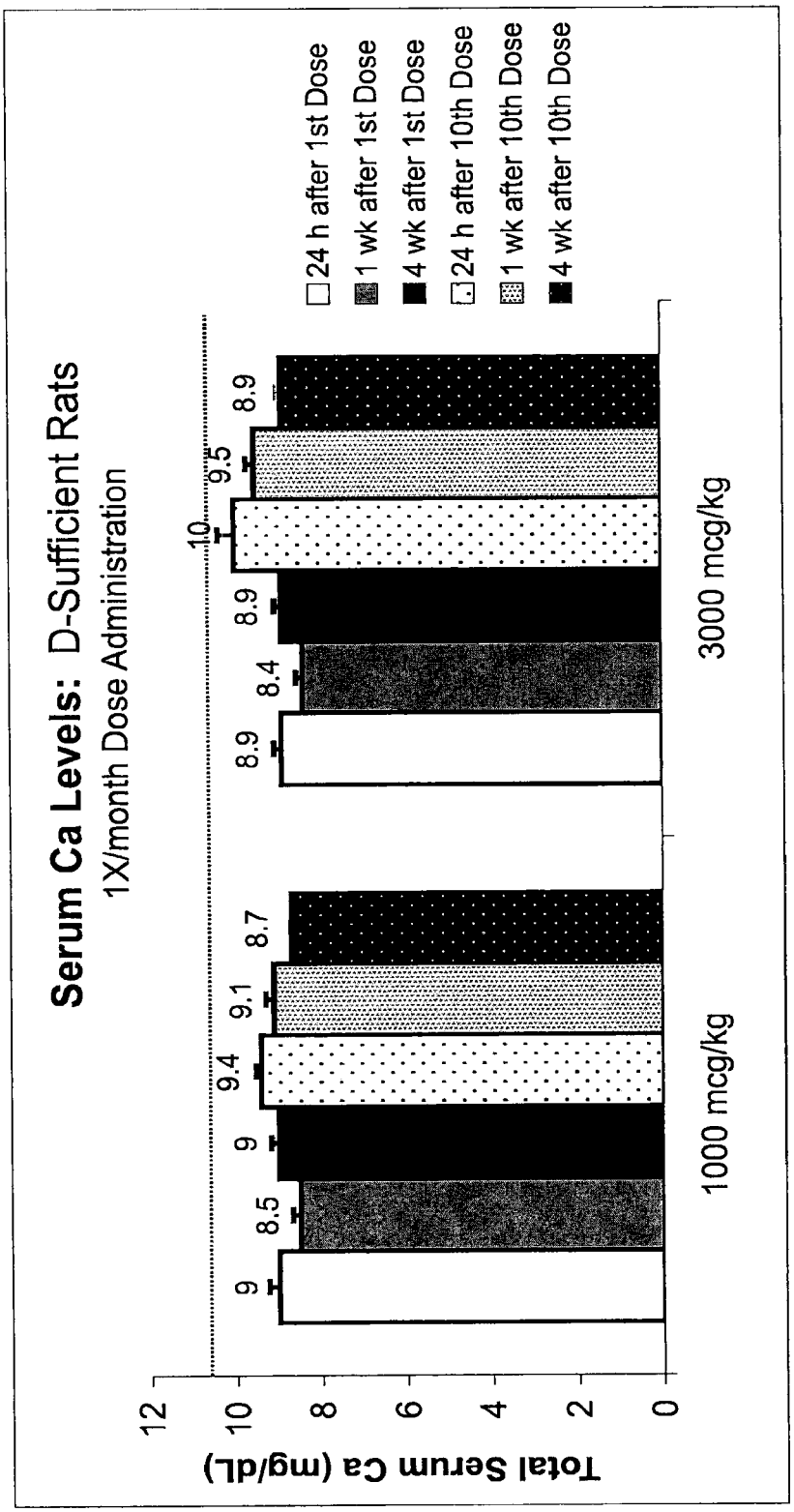
FIG. 6 is a bar graph of serum calcium levels showing no elevations in serum Ca above the normal range (dotted line) occurring after 1×/month dose administration in rats with normal vitamin D status.

FIG. 6 is a bar graph showing no increase in serum calcium outside the normal range (dotted line) occurring after 1×/monthly oral administration of 25(OH)D$_3$ in rats with normal vitamin D status. The rats were male, Sprague-Dawley rats (9 weeks of age, n=4-6 animals/group) received from a commercial supplier. The animals were placed on a purified diet containing 0.47% calcium and allowed to acclimate for one week. After one week the animals were randomly assigned to 3 groups and then orally dosed 1× every 28 days with vehicle (5% ethanol in Neobee oil) or 25(OH)D$_3$ dissolved in ethanol and Neobee oil, whereby blood was collected at the times indicated in the graph. Total calcium concentrations were assessed in the serum using atomic absorption spectrometry or a clinical analyzer (Pentra 400, Horiba ABX Diagnostics—France).

Figure 7:
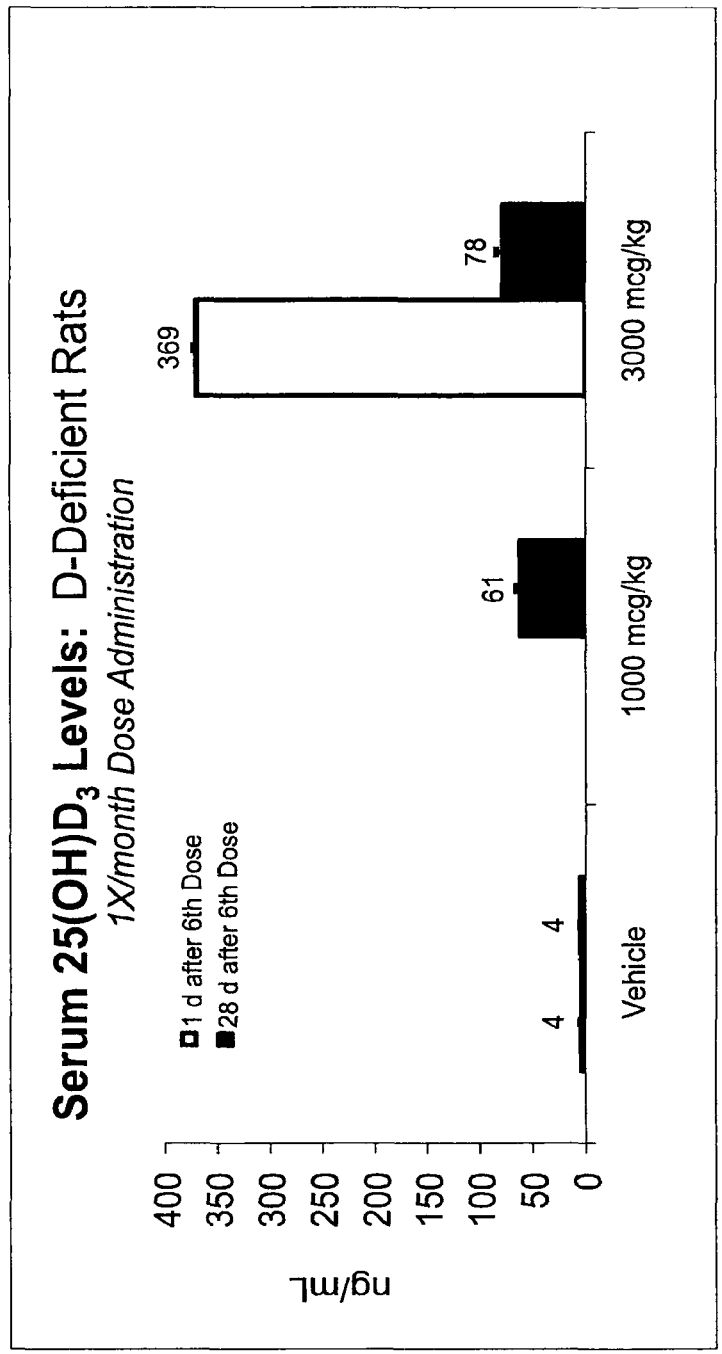
FIG. 7 is a bar graph showing that higher doses of 25(OH)$D_3$ given to D-deficient rats results in circulating levels higher than normal.

FIG. 7 is a bar graph illustrating the increases in serum 25(OH)D$_3$ occurring after 1×/monthly oral administration of 25(OH)D$_3$ at 1000 and 3000 mcg/kg body weight in vitamin D deficient rats. The rats were male, Sprague-Dawley rats (weanlings, n=4-6/group) received from a commercial supplier, whereby the animals were placed in rooms that lacked light emissions in the UV range. The animals were fed diets lacking any vitamin D. At 10 weeks of age the animals were randomly assigned to 3 groups, and then orally dosed 1× every 28 days with vehicle (5% ethanol in Neobee oil) or 25(OH)D$_3$ dissolved in ethanol and Neobee oil. Blood was collected at the times indicated in the graph and serum 25(OH)D$_3$ concentrations were assessed using a commercially available RIA kit (DiaSorin of Stillwater, Minn.).

Figure 8:
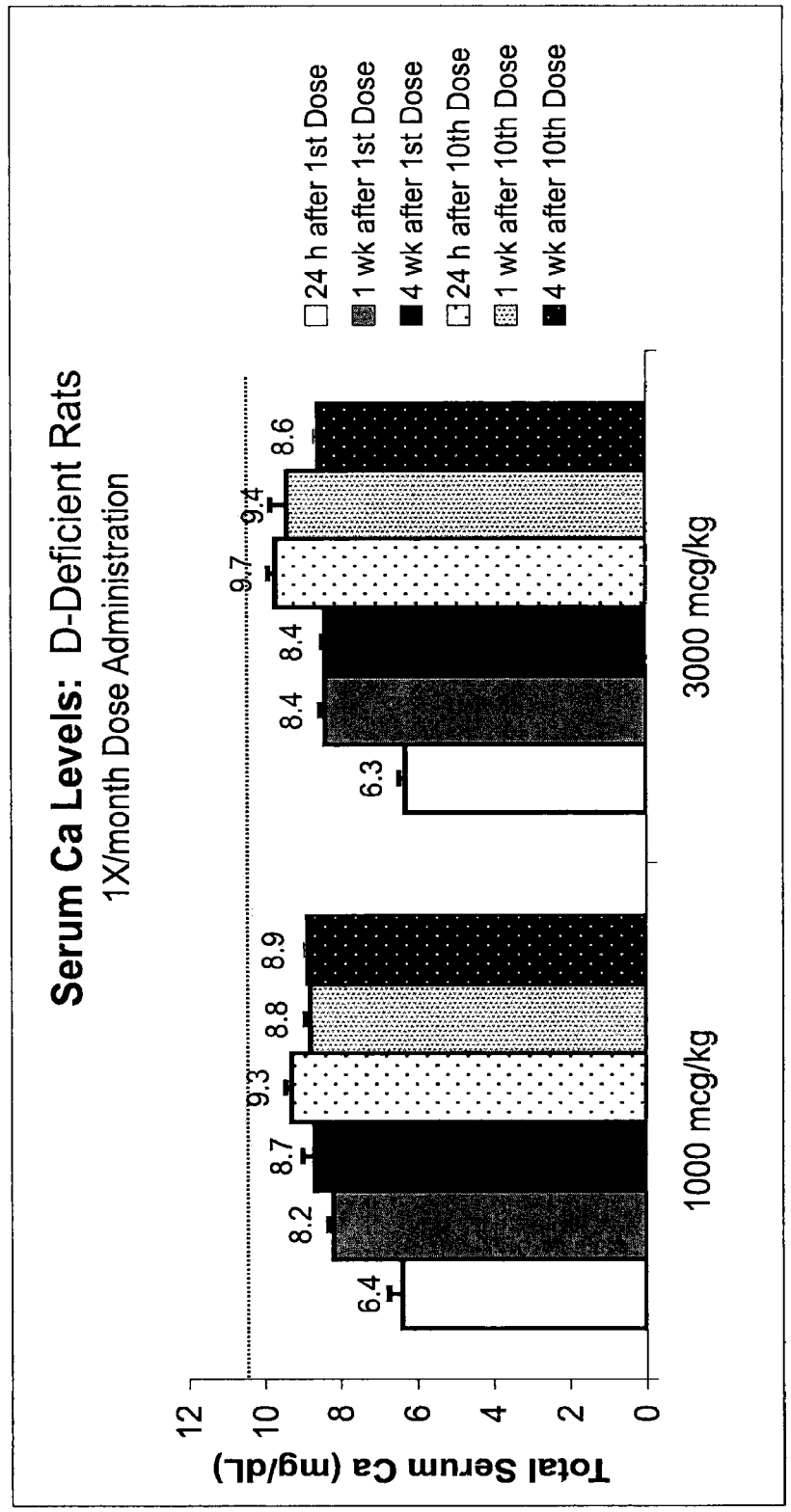
FIG. 8 is a bar graph of serum calcium levels showing no elevations in serum Ca above the normal range (dotted line) occurring after 1×/month dose administration in vitamin D-deficient rats.

FIG. 8 is a bar graph showing no increase in serum calcium outside the normal range (dotted line) occurring after 1×/monthly oral administration of 25(OH)D$_3$ in vitamin D deficient rats. The rats were male, Sprague-Dawley rats (weanlings, n=4-6/group) received from a commercial supplier. The animals were placed in rooms that lacked light emissions in the UV range, whereby the animals were fed diets lacking any vitamin D. At 10 weeks of age the animals were randomly assigned to 3 groups, and then orally dosed 1× every 28 days with vehicle (5% ethanol in Neobee oil) or 25(OH)D$_3$ dissolved in ethanol and Neobee oil. Blood was collected at the times indicated in the graph and total calcium concentrations were assessed in the serum using atomic absorption spectrometry or a clinical analyzer (Pentra 400, Horiba ABX Diagnostics—France).

FIG. 9 is a bar graph illustrating the increases in serum 25(OH)D$_3$ occurring after 1×/weekly oral administration of 25(OH)D$_3$ at 100, 1000 and 3000 mcg/kg body weight in vitamin D deficient rats. The rats were male, Sprague-Dawley rats (weanlings, n=4-6/group) received from a commercial supplier. The animals were placed in rooms that lacked light emissions in the UV range. The animals were fed diets lacking any vitamin D, whereby at 10 weeks of age the animals were randomly assigned to 3 groups and then orally dosed 1× every 7 days with vehicle (5% ethanol in Neobee oil) or 25(OH)D$_3$ dissolved in ethanol and Neobee oil. Blood was collected at the times indicated in the graph and serum 25(OH)D$_3$ concentrations were assessed using a commercially available RIA kit (DiaSorin of Stillwater, Minn.).

FIG. 10 is a bar graph showing no increase in serum calcium outside the normal range (dotted line) occurring after 1×/weekly oral administration of 25(OH)D$_3$ in vitamin D deficient rats. The rats were male, Sprague-Dawley rats (weanlings, n=4-6/group) received from a commercial supplier. The animals were placed in rooms that lacked light emissions in the UV range. The animals were fed diets lacking any vitamin D. At 10 weeks of age the animals were randomly assigned to 3 groups, and then orally dosed 1× every 7 days with vehicle (5% ethanol in Neobee oil) or 25(OH)D$_3$ dissolved in ethanol and Neobee oil. Blood was collected at the times indicated in the graph and total calcium concentrations were assessed in the serum using atomic absorption spectrometry or a clinical analyzer (Pentra 400, Horiba ABX Diagnostics—France).

In summary, FIG. 5 and FIG. 7 show that higher doses of 25(OH)D$_3$ given to D-sufficient and D-deficient rats results in circulating levels higher than normal; however, there are large spikes over the course of 28 days. FIG. 6 and FIG. 8 show that these doses are safe in terms of serum calcium levels. FIG. 9 shows that 1× weekly dosing results in blood levels of >25 (OH)D$_3$ that are above the normal range without the large fluctuations observed when given 1×/monthly and FIG. 10 shows that the 1× weekly dosing regimen is safe in that serum calcium levels do not rise above normal levels.

We claim:

1. An oral dosage form comprising:
   a single dose of 25-hydroxy-vitamin $D_3$, or the monohydrate thereof, sufficient to maintain the serum level in a human in need thereof to a therapeutic concentration in the range of 30 ng/ml to 200 ng/ml for at least 7 days at steady-state pharmacokinetics, and,
   a pharmaceutically suitable oral carrier system.

2. The oral dosage form of claim 1, wherein each single dose administered weekly is sufficient to maintain the serum level in the human to a therapeutic concentration in the range of 30 ng/ml to 200 ng/ml at steady-state pharmacokinetics.

3. The oral dosage form of claim 1, wherein the therapeutic concentration is in the range of 30 ng/ml to 100 ng/ml.

4. The oral dosage form of claim 1 in the form of a soft gel capsule.

5. The oral dosage form of claim 1, wherein the pharmaceutically suitable carrier system comprises one or more digestible oils.

6. The oral dosage form of claim 1 in the form of a tablet.

7. The oral dosage form of claim 1, wherein the single dose is in the range of 10-100 μg/kg body weight of 25-hydroxy-vitamin $D_3$ or the monohydrate thereof.

8. The oral dosage form of claim 1, wherein the single dose is in the range of 30-50 μg/kg body weight of 25-hydroxy-vitamin $D_3$ or the monohydrate thereof.

9. The oral dosage form of claim 1, wherein the single dose is in the range of 0.6 mg-6 mg of 25-hydroxy-vitamin $D_3$ or the monohydrate thereof.

10. An parenteral dosage form comprising:
    a single dose of 25-hydroxy-vitamin $D_3$, or the monohydrate thereof, sufficient to maintain the serum level in a human in need thereof to a therapeutic concentration in the range of 30 ng/ml to 200 ng/ml for at least 7 days at steady-state pharmacokinetics, and,
    a pharmaceutically suitable parenteral carrier system, wherein the parenteral dosage form is an injectable dosage form or an infusion dosage form.

11. The parenteral dosage form of claim 10, wherein each single dose is administered weekly and is sufficient to maintain the serum level in the human to a therapeutic concentration in the range of 30 ng/ml to 200 ng/ml at steady-state pharmacokinetics.

12. The parenteral dosage form of claim 10, wherein the therapeutic concentration is in the range of 30 ng/ml to 100 ng/ml.

13. The parenteral dosage form of claim 10, wherein the single dose is in the range of 10-100 μg/kg of body weight of 25-hydroxy-vitamin $D_3$ or the monohydrate thereof.

14. The parenteral dosage form of claim 10, wherein the single dose is in the range of 30-50 μg/kg of body weight of 25-hydroxy-vitamin $D_3$ or the monohydrate thereof.

15. The parenteral dosage form of claim 10, wherein the single dose is in the range of 0.6 mg-6 mg of 25-hydroxy-vitamin $D_3$ or the monohydrate thereof.

16. A method of maintaining the blood level therapeutic concentration of 25-hydroxy-vitamin $D_3$ at steady-state pharmacokinetics in a human in need thereof comprising orally administering, at least once every 7 days, a single dose of 25-hydroxy-vitamin $D_3$, or the monohydrate thereof, sufficient to maintain the serum level in a human to a therapeutic concentration in the range of 30 ng/ml to 200 ng/ml for at least 7 days at steady-state pharmacokinetics.

17. The method of claim 16, wherein each single dose is administered weekly and is sufficient to maintain the serum level in the human to a therapeutic concentration in the range of 30 ng/ml to 200 ng/ml at steady-state pharmacokinetics.

18. The method of claim 16, wherein the therapeutic concentration is in the range of 30 ng/ml to 100 ng/ml.

19. The method of claim 16, wherein the single dose is in the range of 10-100 μg/kg of body weight of 25-hydroxy-vitamin $D_3$ or the monohydrate thereof.

20. The method of claim 16, wherein the single dose is in the range of 30-50 μg/kg of body weight of 25-hydroxy-vitamin $D_3$ or the monohydrate thereof.

21. The method of claim 16, wherein the single dose is in the range of 35-45 μg/kg of body weight of 25-hydroxy-vitamin $D_3$ or the monohydrate thereof.

22. The method of claim 16, wherein the single dose is in the form of a soft gel capsule or a tablet.

23. The method of claim 16, wherein the human in need thereof is a human deficient in vitamin D having a serum level therapeutic concentration of 25-hydroxy-vitamin $D_3$ less than 30 ng/ml.

24. The method of claim 16, wherein the human in need thereof is a human deficient in vitamin D having a serum level therapeutic concentration of 25-hydroxy-vitamin $D_3$ in the range of 10 ng/ml to 20 ng/ml.

25. A method of maintaining the blood level therapeutic concentration of 25-hydroxy-vitamin $D_3$ at steady-state pharmacokinetics in a human in need thereof comprising parenterally administering by injection or infusion, at least once every 7 days, a single dose of 25-hydroxy-vitamin $D_3$, or the monohydrate thereof, sufficient to maintain the serum level in the human to a therapeutic concentration in the range of 30 ng/ml to 200 ng/ml for at least 7 days at steady-state pharmacokinetics.

26. The method of claim 25, wherein each single dose is administered weekly and is sufficient to maintain the serum level in the human to a therapeutic concentration in the range of 30 ng/ml to 200 ng/ml at steady-state pharmacokinetics.

27. The method of claim 25, wherein the therapeutic concentration is in the range of 30 ng/ml to 100 ng/ml.

28. The method of claim 25, wherein the single dose is in the range of 10-100 μg/kg of body weight of 25-hydroxy-vitamin $D_3$ or the monohydrate thereof.

29. The method of claim 25, wherein the single dose is in the range of 30-50 μg/kg of body weight of 25-hydroxy-vitamin $D_3$ or the monohydrate thereof.

30. The method of claim 25, wherein the single dose is in the range of 35-45 μg/kg of body weight of 25-hydroxy-vitamin $D_3$ or the monohydrate thereof.

31. The method of claim 25, wherein the human in need thereof is deficient in vitamin D having a serum level therapeutic concentration of 25-hydroxy-vitamin $D_3$ less than 30 ng/ml.

32. The method of claim 25, wherein the human in need thereof is deficient in vitamin D having a serum level therapeutic concentration of 25-hydroxy-vitamin $D_3$ in the range of 10 ng/ml to 20 ng/ml.

33. A method of maintaining the blood level therapeutic concentration of 25-hydroxy-vitamin $D_3$ at steady-state pharmacokinetics in a human in need thereof comprising transdermally administering, at least once every 7 days, a single dose of 25-hydroxy-vitamin $D_3$, or the monohydrate thereof, in a transdermal dosage form, sufficient to maintain the serum level in the human to a therapeutic concentration in the range of 30 ng/ml to 200 ng/ml for at least 7 days at steady-state pharmacokinetics.

34. A method of maintaining the blood level therapeutic concentration of 25-hydroxy-vitamin $D_3$ at steady-state pharmacokinetics in a human in need thereof comprising administering by inhalation, at least once every 7 days, a single dose of 25-hydroxy-vitamin $D_3$, or the monohydrate thereof, in an inhalation dosage form, sufficient to maintaining the serum level in the human to a therapeutic concentration in the range of 30 ng/ml to 200 ng/ml for at least 7 days at steady-state pharmacokinetics.

35. A method of maintaining the blood level therapeutic concentration of 25-hydroxy-vitamin $D_3$ at steady-state pharmacokinetics in a human in need thereof comprising administering at least once every 7 days, a single dose of 25-hydroxy-vitamin $D_2$, or the monohydrate thereof, sufficient to maintain the serum level in the human to a therapeutic concentration in the range of 30 ng/ml to 200 ng/ml for at least 7 days at steady-state pharmacokinetics.

36. A dosage form comprising:
a single dose of 25-hydroxy-vitamin $D_2$, or the monohydrate thereof, sufficient to maintain the serum level in a human in need thereof to a therapeutic concentration in the range of 30 ng/ml to 200 ng/ml for at least 7 days at steady-state pharmacokinetics, and, a pharmaceutically suitable carrier system.

37. An inhalation dosage form comprising:
a single dose of 25-hydroxy-vitamin $D_3$, or the monohydrate thereof, sufficient to maintain the serum level in a human in need thereof to a therapeutic concentration in the range of 30 ng/ml to 200 ng/ml for at least 7 days at steady-state pharmacokinetics, and,
a pharmaceutically suitable inhalation carrier system.

38. A topical dosage form comprising:
a single dose of 25-hydroxy-vitamin $D_3$, or the monohydrate thereof, sufficient to maintain the serum level in a human in need thereof to a therapeutic concentration in the range of 30 ng/ml to 200 ng/ml for at least 7 days at steady-state pharmacokinetics, and,
a pharmaceutically suitable topical carrier system.

39. The topical dosage form of claim 38, wherein the dosage is delivered transdermally.

40. The oral dosage form of claim 1, wherein the single dose can elevate the serum level within one day.

41. The oral dosage form of claim 1, wherein the pharmaceutically suitable oral carrier is 5% ethanol in Neobee oil.

* * * * *